United States Patent [19]

Chagnon

[11] 4,356,098
[45] Oct. 26, 1982

[54] STABLE FERROFLUID COMPOSITIONS AND METHOD OF MAKING SAME

[75] Inventor: Mark S. Chagnon, Lowell, Mass.

[73] Assignee: Ferrofluidics Corporation, Nashua, N.H.

[21] Appl. No.: 187,317

[22] Filed: Sep. 15, 1980

Related U.S. Application Data

[63] Continuation-in-part of Ser. No. 92,322, Nov. 8, 1979, abandoned.

[51] Int. Cl.$^3$ .......................... C09D 5/23; C10M 3/44
[52] U.S. Cl. ................................ 252/62.51; 252/62.53; 252/49.6; 252/309; 252/572
[58] Field of Search ............... 252/62.51, 62.52, 62.53, 252/309, 573, 49.6, 572

[56] References Cited

U.S. PATENT DOCUMENTS

| | | | |
|---|---|---|---|
| 3,344,066 | 9/1967 | Schiefer et al. | 252/49.6 X |
| 3,531,413 | 9/1970 | Rosensweig | 252/62.62 |
| 3,575,858 | 4/1971 | Adair et al. | 252/49.6 X |
| 3,700,595 | 10/1977 | Kaiser | 252/62.56 |
| 3,843,540 | 10/1974 | Reimers et al. | 252/62.52 |
| 4,011,168 | 3/1977 | Uhlmann | 252/573 X |

FOREIGN PATENT DOCUMENTS 327225  3/1972  U.S.S.R. .......................... 252/62.52

OTHER PUBLICATIONS

Kaiser et al., IEEE Trans. on Magnitics, vol. Mag. 6, No. 3, pp. 694–698 (9/70).
Addendun, Tech. Rept. 1213, 4 pp., 5/9/49.

*Primary Examiner*—F. Edmundson
*Attorney, Agent, or Firm*—Richard P. Crowley

[57] ABSTRACT

A stable liquid composition which comprises a colloidal dispersion of finely-divided particles in a liquid silicone-oil carrier and a dispersing amount of a surfactant, which surfactant comprises a silicone-oil surfactant containing a functional group which forms a chemical bond with the surface of the particles and a tail group which is soluble in the silicone-oil carrier, to provide a stable ferrofluid composition.

23 Claims, No Drawings

STABLE FERROFLUID COMPOSITIONS AND METHOD OF MAKING SAME

REFERENCE TO PRIOR APPLICATION

This application is a continuation-in-part of U.S. patent application Ser. No. 92,322, filed Nov. 8, 1979 (now abandoned).

BACKGROUND OF THE INVENTION

Ferromagnetic liquids commonly are referred to as ferrofluids and typically comprise a colloidal dispersion of finely-divided magnetic particles, such as iron, $\gamma$ $Fe_2O_3$ (hematite), magnetite and combinations thereof, of subdomain size, such as, for example, 10 to 800 Angstroms, and more particularly 50 to 500 Angstroms, dispersed in a liquid through the use of a surfactant-type material. Typically ferrofluids are remarkably unaffected by the presence of applied magnetic fields or by other force fields, and the magnetic particles remain uniformly dispersed throughout the liquid carrier. Ferrofluid compositions are widely known, and typical ferrofluid compositions are described, for example, in U.S. Pat. No. 3,700,595, issued Oct. 24, 1972, and U.S. Pat. No. 3,764,540, issued Oct. 9, 1973, while a particular process for preparing such ferrofluid compositions is described more particularly in U.S. Pat. No. 3,917,538, issued Nov. 4, 1975, which describes a grinding or ball-mill technique for preparing ferrofluid compositions, and U.S. Pat. No. 4,019,994, issued Apr. 26, 1977, describing more particularly a precipitation technique for preparing ferrofluid compositions.

Ferrofluids have been suggested to be prepared using a wide variety of liquid carriers. However, current state-of-the-art ferrofluids typically employ a hydrocarbon carrier or, for example, a diester liquid, such as ethyl-hexyl azelate. Liquid ferrofluids typically comprise a dispersion of colloidal magnetite stabilized by an aliphatic surfactant in a hydrocarbon-liquid carrier, such as, for example, the use of an oleic-acid-type surfactant. These diester ferrofluids have found use in audio-voice-coil-damping and inertia-damping apparatus and for use in bearings and seals. However, the hydrocarbon-based, and particularly the diester-based ferrofluids have been limited in some applications, because of a relatively large change in viscosity as a function of temperature which occurs with such diester-liquid carriers. Generally, diester ferrofluids have been limited to a narrow temperature-operating range of about 0° C. to 90° C.

Silicone oils or esters, for example, have been suggested as liquid carriers in ferrofluid compositions (see, for example, U.S. Pat. No. 3,764,540) and for use in loudspeakers (see U.S. Pat. No. 4,017,694, issued Apr. 12, 1977). However, stable silicone oil-based ferrofluids have been difficult to synthesize in practice and are not, prior to the described invention, generally offered for sale or used in commerce. Past attempts to synthesize silicone oil-based ferrofluids, utilizing such surfactants as oleic acid, which form the stable hydrocarbon-based ferrofluids generally sold, have had a very limited success. With oleic-acid-type surfactants, only silicone-based ferrofluids of very low molecular weights have been prepared with undesirable high evaporation rates of the silicone. In addition, the use of other surfactants also has proven to be unsatisfactory in preparing silicone-based ferrofluids, since such silicone-based fluids have not proven to be stable in a magnetic or gravity field, either during storage or during use.

It would be most desirable to prepare a very stable ferrofluid which exhibits a smaller change in viscosity with temperature range than do the present range of liquid-carrier-based ferrofluids. In particular, the use of silicone oil as a carrier liquid is most desirable, since such silicone-oil ferrofluids would exhibit smaller changes in viscosity with temperature than other classes of liquids and, therefore, permit the application of such silicone-based ferrofluids to be broadened and to be used, particularly, for example, for use in audio-voice-coil-damping, voice-coil cooling, inertia-damping apparatus and sealing vacuum devices. In addition, such silicone-oil-based ferrofluids also would have the advantage of being chemically inert and would provide greater resistance to chemical degradation than ferrofluid compositions, for example, based on diester, and also would exhibit improved; that is, higher, viscosity index.

Therefore, it would be most desirable and important to prepare improved ferrofluids which exhibit small changes in viscosity with temperature changes, and which ferrofluids are chemically inert and stable during storage and use.

SUMMARY OF THE INVENTION

My invention relates to stable, particle-containing liquid compositions and particularly to improved ferrofluid compositions, the method of making the compositions and the use of such compositions. In particular, my method concerns an improved silicone-oil-based ferrofluid composition and a method of making the silicone-oil-based ferrofluid composition. More particularly, my invention is directed to an improved, stable, chemically inert ferrofluid composition having an improved viscosity index, based on the silicone-oil carrier liquid, and the method of making said ferrofluids.

I have found that stable liquid compositions, containing stable dispersions of finely-divided particles dispersed in silicone oil or silicone liquid as a carrier liquid, can be prepared employing a silicone-oil-based surfactant. Where the particles are magnetic particles, the compositions are ferrofluid compositions of high stability, while the use of nonmagnetic particles provides for stable liquid compositions suitable for use as lubricants, dielectric liquids, electronically responsive liquids; for example, electrostatic printing, and for other uses, wherein stable colloidal particle compositions are useful.

I have discovered that stable ferrofluids may be prepared employing silicone oil as a carrier liquid, and which ferrofluids are characterized by a smaller change in viscosity as a function of temperature and, therefore, are particularly suitable for use in voice coils of loudspeakers, microphones, headphones, and the like and in inertia-damping mechanisms employing ferrofluids. My stable silicone-oil-based ferrofluids are prepared employing a surfactant, such as silicone-oil-based surfactant, wherein the silicone-oil surfactant contains a functional group which forms a chemical bond with the surface of the subdomain magnetic particles employed in the ferrofluid, such as, for example, a functional group that is capable of forming a complex, such as a coordination complex, or by entering into a chemical reaction with the surface of the magnetic particles. The silicone-oil surfactant may be the same as or different from the silicone oil of the ferrofluid carrier, but preferably is of the same general structure, which results in a stable dispersion of the coated magnetic particles in the ferrofluid in the silicone-oil carrier liquid, since the functional head group provides for a bond with the magnetic particles, while the remaining portion of the surfactant molecule is solubilized in the silicone-oil carrier liquid.

The stable ferrofluids of my invention are stable during storage or when subjected to a magnetic-force field or other force fields and, therefore, may be employed in applications which, in the past, have been limited, due to large changes in viscosity as a function of temperature, the lack of chemical inertness or the lack of stability of the ferrofluid.

My invention comprises a stable ferrofluid composition, and particularly those ferrofluid compositions accompanied by a small change in viscosity as a function of temperature, which ferrofluid comprises finely-divided magnetic particles, typically, for example, less than 800 Angstroms; for example, 20 to 500 Angstroms, and more particularly 50 to 150 Angstroms in particle size, colloidally dispersed in a silicone-oil or ester-type carrier liquid and a small, but effective, amount of a silicone-type surfactant, typically a silicone-oil surfactant, wherein the surfactant contains a functional group which forms a chemical bond, such as forming a complex or reactant with the surface of the magnetic particles. My invention also is directed to a method of preparing the improved stable ferrofluids, wherein a silicone oil is employed as the liquid carrier, either through a grinding, precipitating or other technique of preparing ferrofluids, and a silicone-type surfactant is employed containing a reactive functional group in the preparation of the ferrofluid composition.

In general, my invention relates to the use of surfactants, typically organosilicone surfactants, to produce gravitationally and magnetically stable ferrofluid compositions, wherein magnetic particles can be dispersed in a liquid carrier. The surfactants used may have the general structural formula:

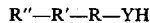

and contain a functional reactive group which has an active hydrogen and which reacts or forms a chemical complex or bond with the surface of the magnetic particles, such as the iron atoms of the activated finely-divided magnetic particles. The YH head or polar group is separated by and linked to an R group (which is optional) which is linked to an R' group. The R' group, typically an organic group, is of sufficient length and rigidity to separate the polar head group YH from the R" tail portion of the surfactant. R' and R may be the same or different groups. The R" group is selected to be soluble in and generally is the same or similar in chemical structure and/or properties as the carrier liquid, so that the R" group will be a a carrier-soluble tail with the polar head group YH attached to the magnetic particles.

The surfactants of choice will be illustrated in use for the preparation of silicone-oil, carrier-liquid, ferrofluid compositions; however, it is recognized that other surfactants of the general type described may be employed with a matching liquid carrier, to provide a wide variety of stable ferrofluid compositions.

The term "silicone oil" is a well-known term and, for the purpose of this invention as a surfactant, comprises a liquid material of a linear polymeric structure derived from siloxane by the substitution of various organic groups for the oxygen atoms in the siloxane, wherein the silicone is bonded to at least one oxygen atom in the chain, and typically such silicone oil is stable over a particular range of, for example, −50° C. to 250° C., with very low viscosity change with temperature. The term "silicone oil" is intended to include silicone esters or other liquid silicone compounds with the above general characteristics and properties. A typical formula of a silicone oil is:

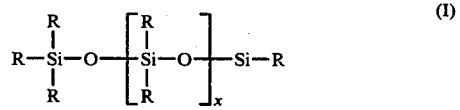

wherein R may be an aliphatic group, such as an alkyl group, preferably a methyl, ethyl or propyl radical or alkoxy group or a phenyl group, but typically R is a phenyl group or a methyl group, or combinations thereof. Typical liquid silicone oils having a low viscosity index; for example, 1 to 20 cps, include, but are not limited to: polydimethyl siloxane; polymethylphenyl siloxane; polydipropyl siloxane; polyphenyl siloxane; and other liquid silicone oils where there is a linear silicone-oxygen backbone, and wherein x has a value of from 100 to 10,000, and more particularly from about 200 to 2000.

The silicone oil as used for the carrier liquid may comprise any liquid organosilicone material, while the silicone oil employed as the surfactant must exhibit surfactant properties and be capable of forming a bond with the magnetic particles and be soluble in the carrier liquid.

Where the particles employed in the stable compositions of the invention are nonmagnetic colloidal particles, the particles may comprise, but not be limited to, metal oxides and sulfides or other particles which have or contain reactive groups, such as sulfur or oxygen groups, thereon, such as adsorbed oxygen, which oxygen groups react with the functional group of the silicone-oil surfactant, such as carbon particles, to prepare a dielectric liquid composition. Typical metal oxides and sulfides include those transition metals, such as those metals having an incomplete d orbital, as well as metals of group VI(b), such as the oxides and sulfides of molybdenum, copper, zinc, nickel, cobalt, tin, cadmium, zirconium, iron, titanium, tungsten, chromium and the like. Stable silicone-oil compositions may be prepared with molybdenum sulfide, copper sulfide, nickel sulfide, zinc sulfide and zinc oxide and sulfur for use as electronically responsive compositions or lubricants, ferrous oxide, titanium oxide and zinc oxide for stable pigment compositions, and carbon, including graphite and carbon black, for dielectric compositions. The liquid compositions may be prepared in the same manner as the preparation of the improved ferrofluid compositions of the invention.

The magnetic particles employed in the ferrofluid may be those typical magnetic particles, either prepared by grinding or precipitation, but typically are finely-divided magnetizable particles usually recognized as magnetite, such as magnetite gamma iron oxide, chromium dioxide, ferrites and similar materials, and which materials also may include various elements and metallic alloys. The preferred materials are magnetite, gamma iron oxide ($Fe_3O_4$) and ($\alpha Fe_2O_3$), wherein the magnetic particles are present usually in an amount of from about 1% to 20%; for example, 2% to 12%, by volume of the ferrofluid.

The surfactant or stabilizing agents employed, in preparing my improved ferrofluid, include those silicone surfactants or surface-active materials which include at least polar-reactive or -functioning groups and a long-chain silicone-oil tail. Typically, the surfactant may be present in an amount sufficient to provide the desired colloidal dispersion and stability to the ferrofluid composition, and more typically is used in a ratio of surfactant-to-magnetic-particles of from about 2:1 to 20:1 by volume; for example, 1:1 to 5:1 by volume. If desired and applicable, the silicone-oil liquid carrier may be used alone or in conjunction with other liquid-carrier materials or other additive materials, and the surfactant employed may be used alone or in combination with other types of surfactants where necessary or required, such as those carboxylic acids or other dispersants or surface-active agents useful in dispersing magnetite particles.

The silicone-oil-type surfactants useful in preparing my improved ferrofluids are shown in the general formula as follows:

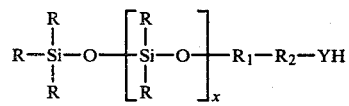
(II)

wherein $R_1$ may be any type of a group, such as an aliphatic, aromatic, inorganic or a silicone-linking group, of sufficient length to separate the solubilizing head group; for example, composed of:

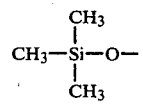

from the YH reacting group and which has sufficient rigidity to direct the YH group toward the magnetite particles.

The silicone-oil surfactants, employed as the surfactants and dispersing agents in my invention with a silicone-oil carrier fluid, are adapted to provide for a functional group within the silicone-oil surfactant, but typically at one end thereof, as illustrated, that is capable of reacting with the high-energy-level iron on the surface of the magnetite particles. The chemical bonding in the YH group or reaction may be the formation of a coordinational complex or the entering into a chemical reaction to form a chemical bond with the iron on the surface of the magnetite particles.

$R_2$ may be an aliphatic, aromatic, inorganic or silicone-linking group or radical whose presence is dependent on the nature of $R_1$, and whose function is to link or separate $R_1$ from the YH reactive group. The YH reactive group may be composed of one or more representative reactive or polar groups which typically include, but are not limited to: carboxylic acids (R—COOH), amines (R—NH$_2$), mercaptans (R—SH), aldehydes

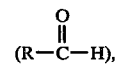

alcohols (R—OH) and other compounds with active hydrogens.

Thus, in practice, the solubilizing or tail groups of the silicone-oil surfactant permit a very stable dispersion by being solubilized easily in the silicone-oil carrier liquid, while the opposite end of the reacting group is secured or chemically bonded to the magnetite particles. The silicone-oil surfactant may be the same as or different from the silicone-oil carrier fluid, either in molecular weight, viscosity, chain length or isometric chemical characteristics. In one preferred embodiment, $R_1$ comprises an Si—CH$_2$, and the YH group comprises an SH or SH$_2$ mercaptan-type group.

Typical and specific formulas of surfactant-active silicone-oil agents, which may be employed in the preparation of my improved ferrofluid, include, but are not limited to the following:

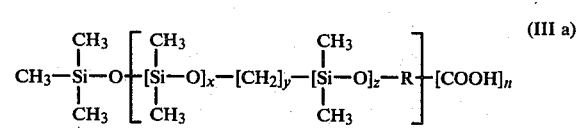
(III a)

wherein n = 1–3
x = 1–100
y = 1–100
z = 1–100

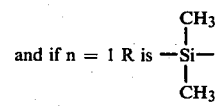
and if n = 1 R is

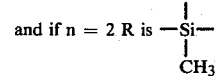
and if n = 2 R is

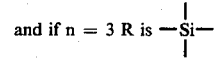
and if n = 3 R is

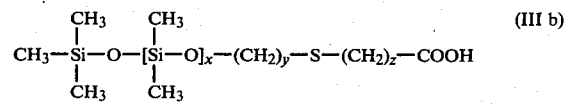
(III b)

wherein x = 1–1000
y = 4–10
z = 4–6

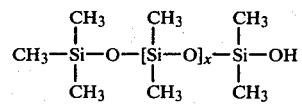
(III c)

mono, di or tri hydroxy-terminated siloxanes

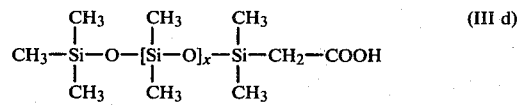
(III d)

carboxylated siloxane prepared by a Grignard reaction of chlorodimethyl polysiloxane over metal then dry ice -continued

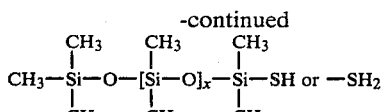

mercaptopolydimethyl siloxane

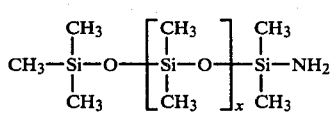

As set forth above, the silicone-oil surfactants may comprise, for example, polydimethyl siloxane omega mono, di or tri carboxylic acids; polydimethyl siloxane alkylene (for example, methylene); mercapto alkylene (for example, methylene) mono, di or tri carboxylic acids; polydimethyl siloxane mono, di or tri hydroxy; polydimethyl siloxane omega mono, di or tri amino; polydimethyl siloxane alkylene (for example, methylene) mono, di or tri carboxylic acid; and polydimethyl siloxane omega mercapto. The surfactant, rather than being polydimethyl, may be a polyalkyl; for example, $C_1$–$C_4$, a polyphenyl or a mixed polyalkyl-phenyl siloxane. The most preferred silicone-oil surfactants are those with a carboxyl group and/or a mercapto group and having an active hydrogen, so that a reaction and coordination complex occurs with the iron of the activated magnetite.

Stable ferrofluid compositions may be prepared in silicone oils, for example, in polydimethyl siloxane or polymethylphenyl siloxane as liquid carriers, by grinding the magnetite in a ball mill in a solution of the silicone-oil surfactant and a solvent, such as a volatile organic solvent, and reacting the activated magnetite with the reactive groups of the silicone-oil surfactant in the solvent slurry, such as, for example, where the solvent is methylethyl ketone, acetone and a hydrocarbon like xylene, toluene or other solvent.

Typical formulations for a grinding operation are:

| | |
|---|---|
| $Fe_3O_4$ | 10–300 gm |
| Surfactant | 2–100 gm |
| Solvent | 100–2000 ml |

After grinding for sufficient time to disperse the magnetite, the colloidal suspension of magnetite, surfactant and grinding solvent is removed from the ball mill. Separation of the surfactant-coated particles from the solvent may be achieved by evaporation or flocculation with acetone or other polar solvent. The sedimentated material is easily solubilized by a liquid polydimethyl siloxane as a carrier liquid.

| | |
|---|---|
| Activated magnetite | 10–100 gm |
| Surfactant | 10–100 gm |
| Acetone | 100–1000 ml |

The activated magnetite is slurried in acetone for 5 to 30 minutes. The surfactant is slowly added to the slurry during constant stirring. A material, that consists of surfactant-coated particles, precipitates from the solution, which material is readily soluble in polydimethyl siloxane as a carrier liquid.

The silicone-oil surfactants of my invention may be employed not only with organosilicone carrier liquids, but with other carrier liquids where the surfactants are soluble.

For the purpose of illustration only, my invention will be described in connection with certain ferrofluids; however, it is recognized that those persons skilled in the art may make various changes and modifications in the ferrofluid compositions and the method of preparing same, all without departing from the spirit and scope of my invention.

DESCRIPTION OF THE EMBODIMENTS

Example 1

Activated magnetite ($Fe_3O_4$) particles were prepared as follows: 260 grams $FeSO_4$, 460 ml 46% $FeCl_3$ and 100 ml water were mixed to dissolve the salts.

800 grams of ice were added to obtain a temperature of $-3°$ C. $Fe_3O_4$ was precipitated from the solution by the slow addition of a solution of 600 ml concentrated $NH_4OH$ and 400 cc water cooled to $+1°$ C. The $Fe_3O_4$ was magnetically separated from the salt/ammoniacal solution and was washed with 200-ml portions of hot water, 100-ml portions of acetone and 200-ml portions of xylene and was vacuum dried.

The activated magnetite prepared in this or a similar manner was then used in the preparation of silicone-oil ferrofluid compositions.

Example 2

A ferrofluid composition of my invention was prepared by the precipitation method by slurrying 80 gm of the activated magnetite, 50 ml of acetone and 50 gm of the silicone-oil surfactant of III(a), also known as GEXf 38-2216 Acid #84 (General Electric Silicone Division). The slurry was mixed in a blender for 3 minutes, and, thereafter, 20 ml of silicone-oil surfactant III(b), also known as DC X27119 (Dow Corning Corporation), were added and the slurry was then again dispersed using the blender for an additional 3 minutes. The resulting dispersed liquid was then poured into a 500-ml beaker, and the solids were allowed to separate on a magnet and the acetone decanted. An additional 20 ml of the silicone-oil surfactant III(b) were added, and the solids were again stirred with 50 cc of acetone. Thereafter, 10 ml of concentrated ammonium hydroxide were then added to the acetone slurry, and a rubbery black material, that was strongly magnetic, representing the silicone-oil-surfactant-coated magnetite particles, was precipitated from the solution. The ammonium and acetone solution was decanted and discarded. The recovered solids were then dispersed in 20 ml of polydimethyl siloxane (Dow Corning—200) as a carrier liquid in a blender. The resulting ferrofluid composition is characterized by a 100 gauss in a viscosity of 1000 cp. The improved ferrofluid composition was stable in a magnetic field.

Example 3

40 gm of the activated magnetite were added to 20 gm of silicone-oil surfactant III(b), and 50 cc of acetone were then stirred and dispersed with a laboratory stirrer. After dispersion for 30 minutes, the resulting material was magnetically separated and the acetone was decantered. An additional 50 cc of acetone were then added to the material, and the dispersion and separation steps were carried out again. A polydimethyl silicone of 1 to 10 cps was then added to the suspension and stirred for about 1 hour, to provide an improved ferrofluid composition having a 500 gauss and approximately 1500 cp.

Example 4

An improved ferrofluid composition was prepared by a grinding technique which employed grinding 20 gm of activated magnetite in the presence of 100 ml of xylene as a solvent and 20 gm of a dicarboxylic-acid silicone-oil surfactant III(a) for approximately 20 days. A viscous tea-colored material was formed and a methylphenyl polysiloxane was added as the carrier liquid.

Example 5

An improved ferrofluid composition was prepared employing, as the silicone-oil surfactant, the mercaptopolydimethyl siloxane III(e), and an improved, stable, ferrofluid composition was recovered.

Example 6

Stable liquid compositions, with silicone oil as the carrier liquid, and colloidal particles of molybdenum sulfide, copper sulfide, nickel sulfide, alumina, titanium dioxide, zinc oxide and carbon-black particles were prepared in a similar manner as set forth in Examples 1–5, substituting the other particles for the magnetic particles.

What I claim is:

1. A stable ferrofluid composition which comprises a colloidal dispersion of finely-divided magnetic particles in a liquid silicone-oil carrier and a dispersing amount of a surfactant, which surfactant comprises a silicone-oil surfactant containing a functional group which forms a chemical bond with the surface of the magnetic particles and a tail group which is soluble in the silicone-oil carrier, to provide a stable ferrofluid composition.

2. The ferrofluid composition of claim 1 wherein the ratio of silicone-oil surfactant to magnetic particles comprises from 2:1 to 20:1 by volume.

3. The ferrofluid composition of claim 1 wherein the magnetic particles are activated magnetite particles.

4. The ferrofluid composition of claim 1 wherein the silicone-oil carrier comprises a polyalkyl-, polyphenyl- or polyalkylphenyl-substituted linear siloxane.

5. The ferrofluid composition of claim 1 wherein the silicone-oil carrier comprises a polydimethyl siloxane, a polyphenylmethyl siloxane or a polyphenyl siloxane.

6. The ferrofluid composition of claim 1 wherein the silicone-oil carrier has a viscosity of from about 10 to 1500 cp.

7. The ferrofluid composition of claim 1 wherein the functional group of the silicone-oil surfactant comprises a carboxylic, amine, mercaptan, aldehyde or alcohol group reactive with the surface of the magnetic particles.

8. The ferrofluid composition of claim 1 wherein the silicone-oil surfactant includes a mercapto functional group.

9. The ferrofluid composition of claim 1 wherein the silicone-oil surfactant comprises a polymethyl siloxane having a functional reactive group selected from the group consisting of amino, mercapto, hydroxy and carboxylic radicals.

10. The ferrofluid composition of claim 1 wherein the surfactant is a polydimethyl siloxane omega carboxylic acid or mercapto surfactant.

11. The ferrofluid composition of claim 1 wherein the silicone-oil surfactant is selected from the group represented by the following formulas:

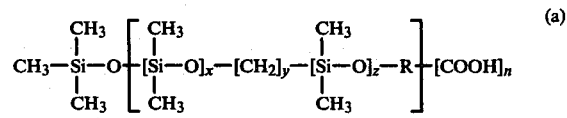

wherein n = 1–3
x = 1–100
y = 1–100
z = 1–100

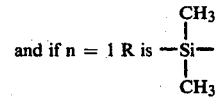

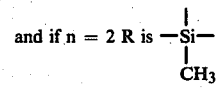

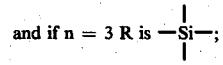

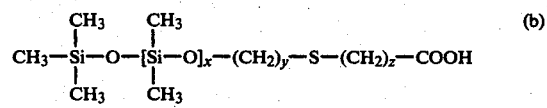

wherein x = 1–1000
y = 4–10
z = 4–6;

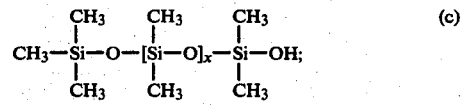

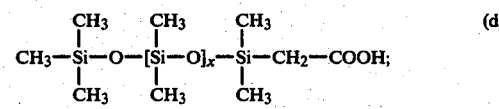

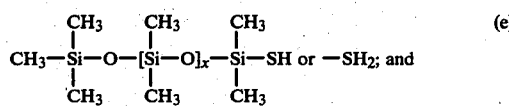

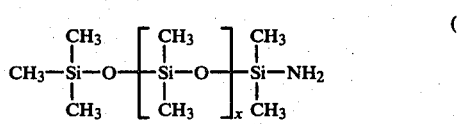

12. The ferrofluid composition of claim 1 wherein the silicone-oil surfactant comprises a carboxy polydimethyl siloxane, a hydroxyl polydimethyl siloxane, a mercapto polydimethyl siloxane, an amino polydimethyl siloxane, a carboxyl polyphenylmethyl siloxane, a hydroxy polyphenylmethyl siloxane, a mercapto polyphenylmethyl siloxane or an amino polyphenylmethyl siloxane.

13. The ferrofluid composition of claim 1 wherein the magnetic particles comprise from about 1% to 20% by volume of the ferrofluid composition.

14. The ferrofluid composition of claim 1 wherein the magnetic particles have a particle size of from about 20 to 500 Angstroms.

15. A stable ferrofluid composition which comprises a colloidal dispersion of finely-divided magnetite particles, having a particle size of less than about 800 Angstroms and comprising from about 1% to 20% by volume of the ferrofluid composition, in a liquid silicone-oil carrier and a dispersing amount of a surfactant, which surfactant comprises a silicone-oil surfactant wherein the ratio of surfactant to magnetite particles comprises from 2:1 to 20:1 volume, and which surfactant contains a functional group which comprises a carboxylic amino, mercapto, aldehyde or alcohol group reactive with the surface of the magnetite particles and which forms a chemical bond with the surface of the magnetite particles and a tail group soluble in the liquid carrier, to provide a stable ferrofluid composition.

16. The ferrofluid composition of claim 15 wherein the silicone-oil surfactant is selected from the group represented by the following formulas:

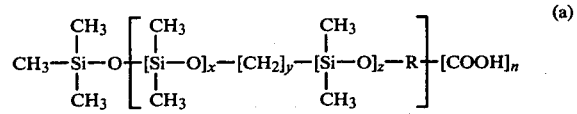 (a)

wherein n = 1–3
x = 1–100
y = 1–100
z = 1–100 and if n = 1 R is 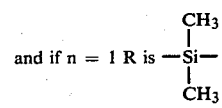

and if n = 2 R is 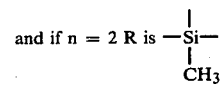

and if n = 3 R is 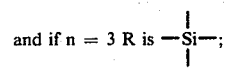;

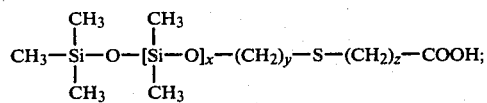 (b)

wherein x = 1–1000
y = 4–10
z = 4–6;

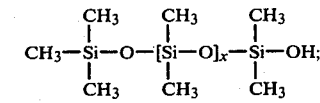 (c)

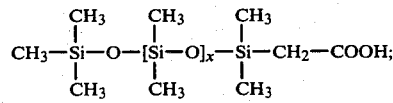 (d)

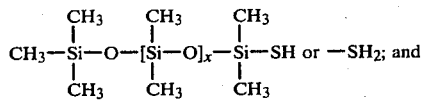 (e)

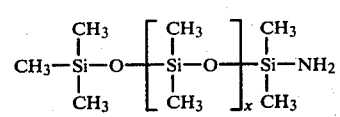 (f)

17. The ferrofluid composition of claim 15 wherein the silicone-oil carrier comprises a polydimethyl siloxane, a polyphenylmethyl siloxane or a polyphenyl siloxane.

18. In a method of preparing a stable ferrofluid composition, which method comprises dispersing finely-divided magnetic particles in a liquid silicone-oil carrier with a dispersing amount of a surfactant to form a colloidal dispersion of a ferrofluid composition, the improvement which comprises employing as the surfactant a silicone-oil surfactant having a functional group reactive with the surface of the magnetic particles during the dispersion, to form a chemical bond with the magnetic particles and to provide a stable silicone-oil ferrofluid composition.

19. The method of claim 18 wherein the ratio of the silicone-oil surfactant to magnetic particles comprises from 2:1 to 20:1 by volume.

20. The method of claim 18 wherein the magnetic particles are activated magnetite particles.

21. The method of claim 18 wherein the silicone-oil carrier comprises a polydimethyl siloxane, a polyphenylmethyl siloxane or a polyphenyl siloxane.

22. The method of claim 18 wherein the silicone-oil carrier has a viscosity of from about 10 to 1500 cp.

23. The method of claim 18 wherein the silicone-oil surfactant is selected from the group represented by the following formulas:

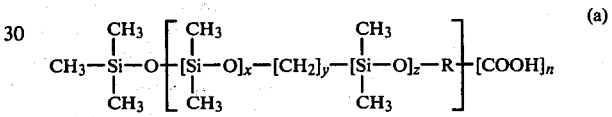 (a)

wherein n = 1–3
x = 1–100
y = 1–100
z = 1–100 and if n = 1 R is 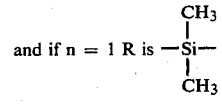

and if n = 2 R is 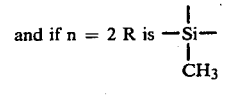

and if n = 3 R is 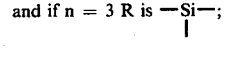;

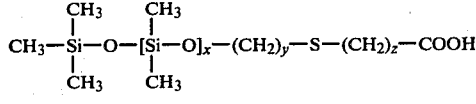 (b)

wherein x = 1–1000
y = 4–10
z = 4–6;

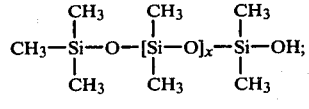 (c)

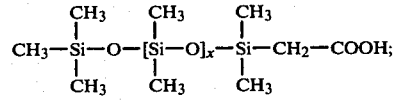 (d)

-continued
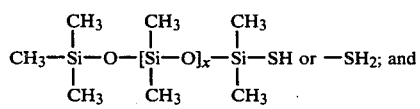 (e)
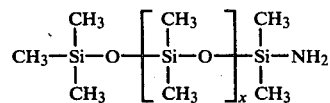 (f)
* * * * *